United States Patent [19]

Manning et al.

[11] 4,276,271

[45] Jun. 30, 1981

[54] PROCESS FOR THE REMOVAL OF HYDROGEN SULFIDE FROM GAS MIXTURES

[75] Inventors: William P. Manning; Stephen J. Rehm; Jeffrey L. Schmuhl, all of Tulsa, Okla.

[73] Assignee: Combustion Engineering, Inc., Windsor, Conn.

[21] Appl. No.: 99,942

[22] Filed: Dec. 3, 1979

Related U.S. Application Data

[63] Continuation-in-part of Ser. No. 8,989, Feb. 5, 1979, abandoned.

[51] Int. Cl.$^3$ .............................................. B01D 53/34
[52] U.S. Cl. .................................... 423/226; 423/225; 423/232; 423/234; 423/220
[58] Field of Search ............... 423/220, 225, 226, 232, 423/234, 561 R, 561 A, 561 B, 622; 252/313 R, 309

[56] References Cited

U.S. PATENT DOCUMENTS

| | | | |
|---|---|---|---|
| 2,215,754 | 9/1940 | Headlee | 423/220 |
| 2,378,689 | 6/1945 | Collins | 423/234 |
| 2,641,527 | 6/1953 | Leutz | 423/226 X |
| 3,957,674 | 5/1976 | Sano et al. | 423/225 X |

OTHER PUBLICATIONS

The Merck Index, Merck Co., Inc. Rahway, N.J. 8th Ed. 1968, p. 960.

*Primary Examiner*—Earl C. Thomas
*Attorney, Agent, or Firm*—Arthur L. Wade

[57] ABSTRACT

An aqueous solution of a zinc salt is used to selectively remove hydrogen sulfide from a gas mixture. An insoluble basic zinc compound is added to the solution to regenerate, or replenish, the salt. A dispersant is added to both decrease the surface tension of the liquid and reduce the degree of hydration of the basic compound, thereby retarding significantly the agglomeration, settling and loss of the basic zinc compound.

3 Claims, 2 Drawing Figures

PROCESS FOR THE REMOVAL OF HYDROGEN SULFIDE FROM GAS MIXTURES

This application is a continuation in part of application Ser. No. 8,989 filed Feb. 5, 1979, and now abandoned.

TECHNICAL FIELD

The present invention relates generally to the prevention of the settling of basic insoluble zinc compounds while they are removing the hydrogen sulfide component of a gas mixture. More particularly, the invention relates to a process in which a zinc salt is converted into the sulfide in the presence of (1) a basic zinc compound to control the pH and replenish the salt, and (2) a dispersant that retards the agglomeration and settling of the basic compound.

BACKGROUND ART

Gas mixtures containing hydrogen sulfide are called "sour" by those skilled in this art. There are many sour natural gas wells whose production is not large enough to justify the cost of a conventional amine system using monoethanolamine in solution with water.

The removal of relatively small amounts of hydrogen sulfide from natural gas without the simultaneous removal of carbon dioxide can be accomplished with the iron sponge process. The sour gas is contacted with hydrated ferric oxide to form ferric sulfide. If regenerated by exposure to air, the ferric sulfide is oxidized to sulfur and ferric oxide which can then be reused. This reaction-regeneration process cannot be repeated indefinitely because the surface of the ferric oxide becomes coated with sulfur.

Shortcomings of the iron sponge process include: (1) incomplete conversion of ferric oxide to ferric sulfide, (2) the pyrophoric nature of ferric sulfide, (3) the labor required to prepare the iron sponge, and (4) the time used to remove the spent iron sponge, particularly when regenerated, and recharge the reaction tower.

It is well known that zinc sulfide is very insoluble. Aqueous solutions of zinc salts combine with hydrogen sulfide to form zinc sulfide. However, as the hydrogen sulfide is absorbed, the pH of the solution decreases, and the point is soon reached where the effectiveness of the solution to absorb hydrogen sulfide is seriously impaired and the danger of corrosion of the metal container increases.

To date, provision, as disclosed in the prior art (eg. U.S. Pat. Nos. 2,378,689 and 2,641,527) to prevent this deleterious decrease in the pH or to replenish the metallic salt as it is consumed, is to add a basic zinc compound. However, these basic zinc compounds are insoluble, have a high specific gravity, tend to agglomerate and settle, and often become coated with sulfide. These phenomena preclude the stoichiometric usage of the basic zinc compound.

DISCLOSURE OF INVENTION

The present invention provides an aqueous solution of a zinc salt in the presence of (1) a zinc compound to control the pH and replenish the salt as it combines with and removes hydrogen sulfide from a mixture of gases, and (2) a dispersant selected from the group including sodium, trisodium, and tetrapotassium polyphosphates; polyphosphonates; polysilicates; polyvinyl pyrolidones and co-polymers; polyacrylates and co-polymers; and co-polymers of maleic anhydride with styrene, vinyl alcohol, or butadiene, that retards the agglomeration and settling of the basic compound.

More specifically, the present invention provides a slurry of an aqueous solution of zinc acetate as the preferred zinc salt, zinc oxide as the preferred basic compound, and sodium hexametaphosphate as the preferred dispersant.

Still more specifically, the invention provides a slurry comprised of (1) 75 to 95% by weight of a solution containing 0.5 to 2.0% of zinc acetate and 0.1 to 1.0% of sodium hexametaphosphate in water and (2) 5 to 25% by weight of zinc oxide. The gas is treated by passing it up through a batch of this slurry. The sodium hexametaphosphate keeps the zinc oxide in suspension so that it is stoichiometrically consumed. When this occurs, the zinc sulfide precipitate is separated from the batch by dencantation or filtration. Fresh zinc oxide is added to the supernatant liquid of the batch to form a fresh slurry with which to continue the treatment of additional sour gas.

Other objects, advantages and features of the invention will become apparent to one skilled in the art upon consideration of the written specification, appended claims, and accompanying drawings.

BEST MODE FOR CARRYING OUT THE INVENTION

In aqueous solution, zinc acetate ionizes and the zinc ions so formed combine readily with hydrogen sulfide when it is bubbled through the solution. However, as the zinc ions are consumed, acetic acid accumulates and the pH decreases. The point is soon reached where hydrogen sulfide is no longer absorbed quantitatively. Also, with the lower pH, the threat of corrosion of the containing metal vessel increases.

The search then began for the preferred basic compound to react with the acetic acid and extend the period of effective hydrogen sulfide absorption. Zinc oxide was selected as the most suitable for this function. The overall process is the conversion of zinc oxide to zinc sulfide.

Carbon dioxide in natural gas mixtures complicates matters because of the tendency to form zinc carbonate which is also insoluble. It is mandatory that any zinc carbonate which may be formed will react with the acetic acid to form zinc acetate and liberate carbon dioxide.

Figure 1:
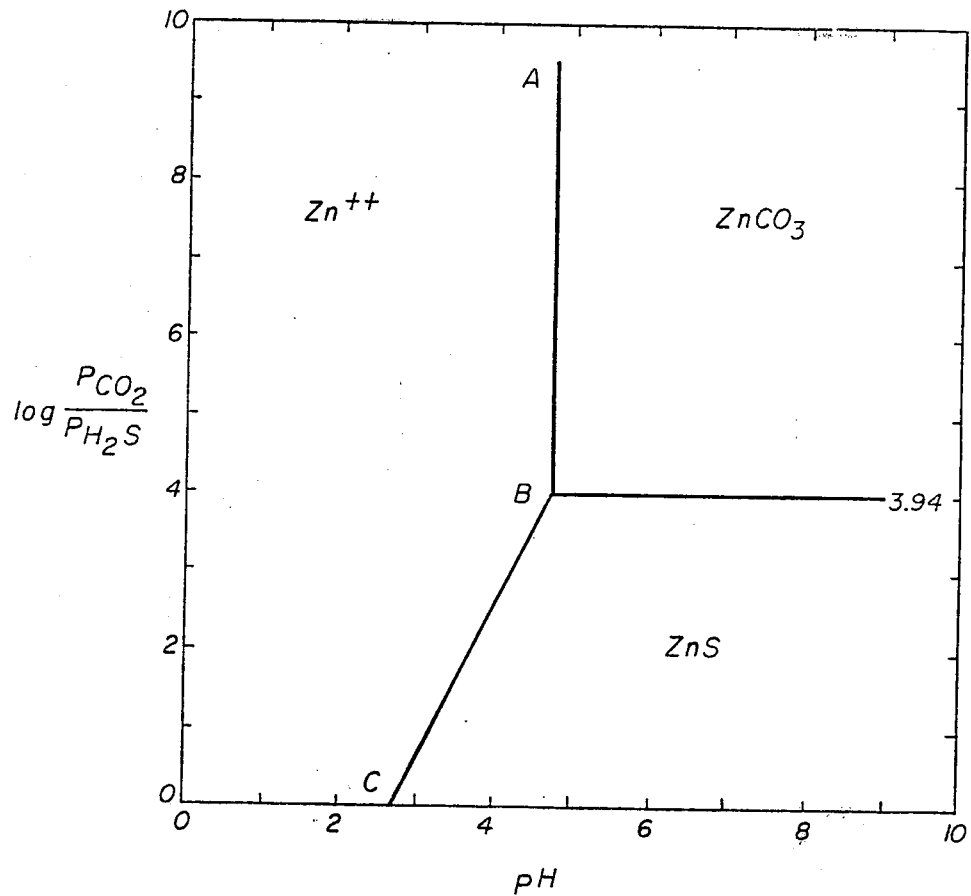
FIG. 1 is the predominance diagram for zinc ions in solution, solid zinc carbonate and solid zinc sulfide, disclosing the pH of the solution and the ratios of partial pressure of carbon dioxide and hydrogen sulfide which define the region in which the invention is reduced to practice.

The operating conditions needed to insure that the process will always remove hydrogen sulfide quantitatively can be illustrated by a predominance diagram. The predominance diagram shown in FIG. 1 gives the range of pH of the slurry and the ratio of the partial pressures of carbon dioxide and hydrogen sulfide contacted by the slurry. This particular diagram was derived for a concentration of zinc ions in solution of 0.1 mol/liter ($Zn^{++} = 0.1$ mol/liter) and a partial pressure for carbon dioxide of 76 mm Hg (P $CO_2 = 76$ mm Hg).

Three regions, or zones, exist:
1. $Zn^{++}$, where neither $H_2S$ nor $CO_2$ is absorbed by the slurry,
2. $ZnCO_3$, where $CO_2$ is absorbed and $H_2S$ is rejected by the slurry, and
3. ZnS, where the $H_2S$ is absorbed and the $CO_2$ rejected by the slurry.

It is obvious that the pH of the slurry must be kept in Region 3, and the presence of the unreacted zinc oxide keeps the pH above those values represented by the line BC.

The major drawback to using the slurry of zinc oxide particles in a zinc acetate solution is that the zinc oxide particles tend to agglomerate and settle to the bottom of the container. This is tantamount to the removal and loss of zinc oxide. Accordingly, the search was extended to find a suitable dispersant that would keep the basic compound in suspension.

In an aqueous slurry, zinc oxide particles hydrate, i.e. water molecules attach to the zinc oxide particles to form larger particles, the surfaces of which are covered with hydroxyl radicals. These hydrated particles coagulate and flocculate into larger particles that settle far more rapidly than the individual particles. This phenomenon is accelerated by divalent zinc ions.

Agglomeration can be reduced significantly by a dispersant which sequesters the zinc ions so that they no longer promote the agglomeration of the zinc oxide particles.

The preferred dispersant must not produce foaming and uncontrolled expansion of the slurry when the gas is bubbled through the slurry. Consequently, detergents such as the sodium salts of aliphatic or aromatic acids and derivatives thereof are not suitable. The dispersant performs three functions. It (1) reduces the surface tension of the liquid, (2) reduces the degree of hydration of the suspended zinc oxide particles, and (3) promotes the uniform suspension of the fine particles of zinc oxide by sequestering the zinc ions in the aqueous solution. The preferred dispersant must be selected from the group including phosphorus as the polyphosphate or polyphosphonate radical and have a molecular weight ranging from 300 to 2000. Specifically, these include sodium, trisodium, and tetrapotassium polyphosphates characterized by carbon-oxygen-phosphorus bonds and polyphosphonates of the Dequest type characterized by carbon-phosphorus bonds. Other suitable dispersants are polysilicates, polyvinyl pyrolidones and co-polymers, polyacrylates and co-polymers, and co-polymers of maleic anhydride with styrene, vinyl alcohol or butadiene.

A similar argument also applies to the suspension of zinc sulfide particles which are precipitated as the monohydrate from aqueous solutions. Indeed the agglomeration of zinc sulfide is particularly troublesome when the natural gas contains mercaptans.

Laboratory Tests

A first test was made to obtain stoichiometric usage of the zinc oxide under conditions which resemble the actual reduction to practice as closely as possible.

The apparatus used was a clear plastic cylinder 1.5 inches ID by 16 inches long. The base of this cylinder included a sparger for introducing the test gas. The head of the cylinder was fitted with orifices for the exit gas, a pressure gauge, and charging the slurry.

A valve in the exit gas line controlled the pressure in the cylinder. The flow of gas was monitored continuously by a rotometer and measured periodically by the displacement of water from a graduated cylinder.

EXAMPLE 1

(A) A slurry was formed of 2.0 gm of zinc acetate, 5.0 gm of zinc oxide, and 250 ml of water. A drop of Union Carbide's SAG 470 antifoamant and two drops of methylred-bromcresyl-green pH indicator were added and the mixture shaken.

(B) The test gas containing 1.6% hydrogen sulfide, 9.9% carbon dioxide, and 88.5% methane was admitted to the test cylinder. The pressure was adjusted to 50 psig and the gas flow rate set to 2.3 liters/min.

(C) The outlet gas was monitored with wet lead acetate paper. When the paper darkened and the indicator turned from blue to red, indicating a pH change from 6 to 4, the test duration was recorded.

(D) The gas was released from the cylinder and another 5.0 gm of zinc oxide added. The steps (A), (B) and (C) were repeated. Consistently, the amount of hydrogen sulfide absorbed by the slurry corresponded to the stoichiometric usage of the zinc oxide. The test for Example 1 was repeated by adding 10% ethylene glycol as antifreeze to the water. The results were not significantly affected.

The test for Example 1 was repeated by adding 1.75 gm of sodium hexametaphosphate as a dispersant to the water. The results were not significantly affected. The purpose of the second test was to determine the effectiveness of the sodium hexametaphosphate in retarding the settling of the zinc oxide.

EXAMPLE 2

Identical 100 ml volumes of two aqueous slurries containing (1) 14.0 gm of zinc oxide and 1.0 gm of zinc acetate, and (2) 14.0 gm of zinc oxide, 1.0 gm of zinc acetate and 1.75 gm of sodium hexametaphosphate were prepared. Sufficient natural gas mixture containing 0.35% hydrogen sulfide was bubbled into the slurries to convert half of the zinc oxide into zinc sulfide. The slurries were then poured into 100 ml graduated cylinders and allowed to stand.

Figure 2:
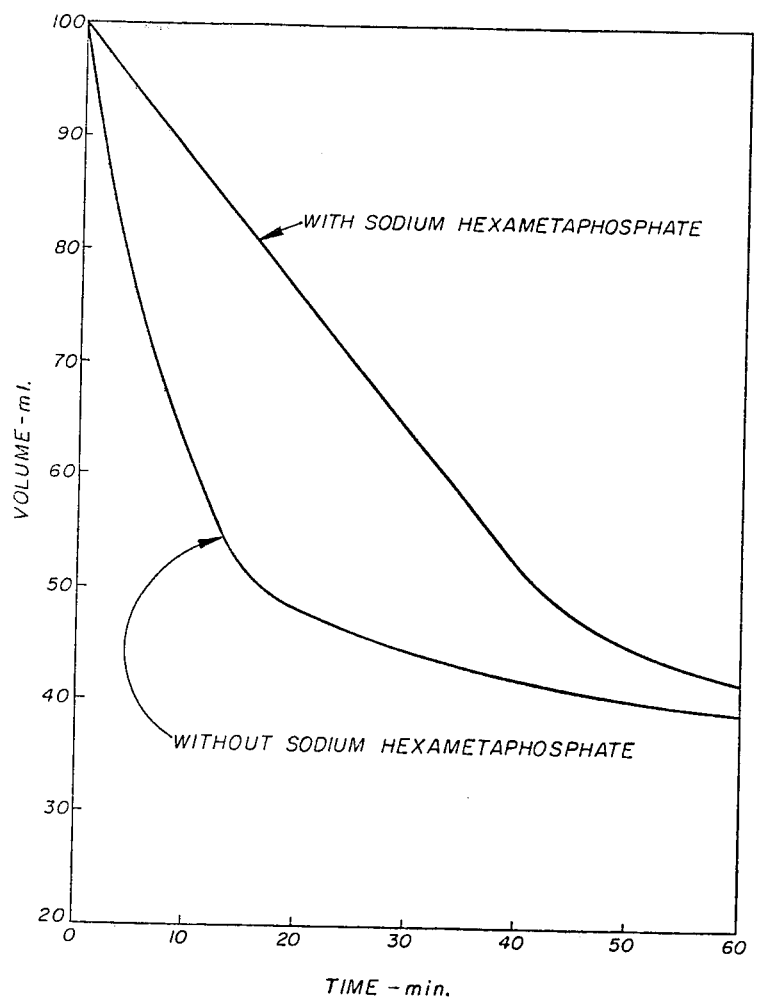
FIG. 2 is a graph of the comparative settling rates of the slurry with and without the dispersant embodied in the invention.

The line of demarcation between the white slurry and the supernatant layer of clear solution was recorded for both cylinders for a period of one hour. These results, shown in FIG. 2, demonstrate the effectiveness of the dispersant. For example, the demarcation line for the slurry without the sodium hexametaphosphate reached the 50 ml mark in 16 minutes. The corresponding time for the slurry with the sodium hexametaphosphate was 46 minutes.

The simplest means of keeping the slurry mixed is to use the force of the rising gas bubbles. This is difficult to accomplish and makes the retardation of particle settling by the dispersant very important. Thus, in actual reduction to practice, it was established without question that the dispersant disclosed was markedly effective in accomplishing the object of the invention.

From the foregoing, it will be seen that this invention is one well adapted to attain all of the ends and objects hereinabove set forth, together with other advantages which are obvious and inherent to the method.

It will be understood that certain features and subcombinations are of utility and may be employed without reference to other features and subcombinations. This is contemplated by and is within the scope of the invention.

As many possible embodiments may be made of the invention without departing from the scope thereof, it is to be understood that all matter herein set forth or shown in the accompanying drawings is to be interpreted in an illustrative and not in a limiting sense.

We claim:

1. A method for removing hydrogen sulfide from a gas mixture by the steps of, forming an aqueous solution from a zinc salt, adding an insoluble basic zinc compound in particulate form to the solution, adding a soluble dispersant selected from the group including sodium, trisodium, and tetrapotassium polyphosphates; polyphosphonates; polysilicates; polyvinyl pyrolidones and co-polymers; polyacrylates and co-polymers; and co-polymers of maleic anhydride with styrene, vinyl alcohol, or butadiene, which will keep the particles of the basic compound in suspension by reducing the surface tension of the solution and the degree of hydration of the particulate matter thereby obtaining stoichiometric usage of the basic compound, and passing a mixture of gas and hydrogen sulfide through the solution for reaction of the hydrogen sulfide with the zinc salt to form zinc sulfide precipitate and free acid while the basic compound addition controls the pH and reforms the salt with the free acid.

2. The method of claim 1 wherein, the zinc salt is zinc acetate, the basic compound is zinc oxide and the soluble dispersant selected is sodium hexametaphosphate.

3. The method of claim 2 wherein, the slurry consists of (1) 75 to 95% by weight of an aqueous solution containing 0.5 to 2.0% of zinc acetate and 0.1 to 1.0% of sodium hexametaphosphate and (2) 5 to 25% by weight of zinc oxide.

* * * * *